US00PP22947P3

(12) United States Plant Patent
Austin

(10) Patent No.: US PP22,947 P3
(45) Date of Patent: Aug. 14, 2012

(54) *ROSA HYBRIDA* SHRUB PLANT NAMED 'AUSBOXER'

(50) Latin Name: *Rosa hybrida*
Varietal Denomination: AUSboxer

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 25 days.

(21) Appl. No.: 13/065,164

(22) Filed: Mar. 14, 2011

(65) Prior Publication Data

US 2012/0144536 P1 Jun. 7, 2012

(30) Foreign Application Priority Data

Dec. 6, 2010 (QZ) ..... PBR 20102727

(51) Int. Cl.
*A01H 5/00* (2006.01)

(52) U.S. Cl. ..... Plt./103; Plt./102; Plt./107

(58) Field of Classification Search ..... Plt./102, Plt./103, 107
See application file for complete search history.

*Primary Examiner* — Susan McCormick Ewoldt
(74) *Attorney, Agent, or Firm* — Kauth, Pomeroy, Peck & Bailey LLP

(57) ABSTRACT

A variety of rose plant of the shrub class, named 'AUSboxer'. The 'AUSboxer' rose is a plant suitable for repeat cut-flower production having rich creamy-white buds with a pink blush and a Myrrh fragrance.

1 Drawing Sheet

Classification: The present invention relates to a new *Rosa hybrida* shrub.

Variety denomination: The new plant has the varietal denomination 'AUSboxer'.

CROSS-REFERENCE TO RELATED APPLICATIONS

The current application claims priority to a European Community Plant Variety Application No. 2010/2727, filed Dec. 6, 2010, the disclosure of which is incorporated by reference.

ORIGIN OF INVENTION

This invention relates to a new and distinct variety of shrub rose plant named 'AUSboxer', which was originated by crossing two unnamed, unpatented varieties of *Rosa hybrida*.

BACKGROUND OF THE INVENTION

The primary objective of this breeding was to produce a rose with blush pink buds, which gradually open to reveal large, many-petalled blooms, which are predominately creamy-white, but delicately brushed with pink, with a Myrrh fragrance, and having a long vase life as a cut rose, produced on strong upright stems, which are suitable for year round cut-flower production under standard greenhouse conditions.

SUMMARY OF THE INVENTION

Among the features which distinguish the new variety from others presently available and commercial rose cultivars known to the inventor is the following combination of characteristics: predominately creamy-white buds that are brushed with pink, and a Myrrh fragrance.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSboxer' may be asexually propagated by budding. The budding successfully occurred on the plant/rootstock *Rosa* cv. 'Inermis.'

COMPARISON WITH PARENTS

The new rose may be distinguished from its seed parent, by the following combination of characteristics: whereas the seed parent is a deep yellow rose with no fragrance, 'AUSboxer' bears a creamy-white bloom with a blush of pink and has a myrrh fragrance.

The new variety may be distinguished from its pollen parent, by the following combination of characteristics: whereas the pollen parent is of a deeper pink with a larger bloom and a powerful fragrance, 'AUSboxer' has a creamy-white bloom with only a blush of pink and has a moderate myrrh fragrance.

COMPARISON WITH THE CLOSEST COMMERCIALLY AVAILABLE CULTIVAR

The closest commercially available cultivar to the new variety is the 'AUSneil' (U.S. Plant Pat. No. 17,317). The new rose may be distinguished from the 'AUSneil' variety by the following combination of characteristics: the 'AUSneil' produces white blooms, but with no pink and fewer petals, compared to 'AUSboxer' which produces creamy-white blooms having a pink blush. In addition, another close cultivar is 'AUSlevel' (U.S. Plant Pat. No. 8,765). The new rose may be distinguished from the 'AUSlevel' variety by the following combination of characteristics: the 'AUSlevel' produces blooms of a similar colour to the 'AUSboxer' shade of creamy-white, but with no pink shading.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown indoors in a greenhouse in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.2 cm long and 1.6 cm in diameter when the petals start to unfurl.

*Form*.—The bud form is pointed ovoid.

*Color*.—When sepals first divide, the bud color is red RHS 37B with yellow-green RHS 145C. When half blown, the upper sides of the petals are red-purple RHS 65D, and the lower sides of the petals are orange RHS 27D.

*Calyx*.—Shape: the calyx opens up into a star-shape, which folds right back against the receptacle and penduncle as the flower opens and ages. Length: 3 cm. Diameter: 3 cm.

*Sepals*.—Arrangement: Regular. Color: Upper Surface: yellow-green RHS 147C. Lower Surface: yellow-green RHS 141C. Length: 3 cm. Width: 9 mm. Shape: Acuminate. Margin: N/A. Surface texture: Upper Surface: Downy. Lower Surface: Smooth. Number: There are three normally appendaged sepals. There are 2 unappendaged sepals with glandular edges.

*Receptacles*.—Color: yellow-green RHS 144B. Shape: funnel. Size: medium, about 0.8 cm×1 cm. Surface: Smooth.

*Peduncle*.—Length: medium, averaging about 5 cm. Surface: smooth. Color: yellow-green RHS 144B. Strength: Strong.

Blooms:

*Size*.—Large, average open diameter is about 9 cm.

*Borne*.—Singly, because variety is grown as a cut flower, and so buds and side shoots are nipped out.

*Stems*.—Strength: Strong, average length is about 45 cm. Diameter: 5 mm.

*Form*.—When first open, bloom is cupped. Permanence of bloom: flattens.

Petalage: Number of petals under normal conditions: 110.

*Color*.—The upper sides of the petals are white RHS N155D with red-purple RHS 65B. The reverse sides of the petals are white RHS N155D with red-purple RHS 64D. The base of the petals has no yellow spot and the white shade RHS N155D.

*Variegations*.—Shading of RHS 64B and 64D at the tips of some petals.

*Discoloration*.—N/A.

*Fragrance*.—Moderate. Character of fragrance: Myrrh.

Petals:

*Texture*.—Smooth.

*Size*.—Width: 3.7 mm. Length: 3.8 mm.

*Surface*.—Smooth.

*Shape*.—Round (mostly) with some outer petals deltoid.

*Margin*.—Irregular.

*Apex shape*.—Rounded.

*Base shape*.—Rounded.

*Form*.—Incurved.

*Arrangement*.—Regular.

*Petaloids*.—Number: 4. Color: white RHS N155D. Length: 7 mm. Width: 4 mm. Shape: Obovate. Margin: Irregular.

*Persistence*.—Petals drop off cleanly before drying.

*Lastingness*.—On the plant: not tested. As a cut flower: long, about 11 days.

Reproductive parts:

*Stamens*.—Number: 25. Length: 9 mm.

*Anthers*.—Length: 2.5 mm. Color: yellow RHS 13A. Arrangement: Regular around styles mixed with few petaloids.

*Filaments*.—Color: yellow RHS 12C. Length: 5 mm.

*Pollen*.—Color: greyed-orange RHS N167A.

*Pistils*.—Number: 35. Length: 15 mm.

*Styles*.—Color: greenish-white with pink, ie greyed-green RHS 193D with red-purple RHS 65B. Length: 9 mm.

*Stigmas*.—Color: greyed-green RHS 193D. Length: 11 mm.

*Hips*.—None Observed.

PLANT CHARACTERISTICS

Plant form: Shrub.

Plant growth: Upright.

Age to maturity: One year.

Mature plant: Height: 110 cm. Width: 85 cm.

Rootstock: *Rosa* 'Inermis' for observed plants.

Foliage:

*Number*.—Leaflets on normal mid-stem leaves is: 5 (including terminal leaflet).

*Size*.—Medium, about 14 cm long×9 cm wide.

*Quantity*.—Normal. Number of leaves per flowering stem is: 10.

*Color*.—New foliage: Upper side: green RHS 137C with red-purple RHS 59B. Lower side: red-purple RHS 59B. Old foliage: Upper side: green RHS 139A. Lower side: green RHS 138B.

Leaflets:

*Size*.—About 5 cm long×4 cm wide.

*Shape*.—Broadly oval.

*Base shape*.—Rounded.

*Apex shape*.—Cuspidate.

*Texture*.—Smooth.

*Edge*.—Serrated.

*Serrations*.—Single.

*Petiole*.—Color: green RHS 137A. Length: 3 cm. Width: 1.5 mm. Surface Texture: Smooth.

*Petiole rachis*.—Color: green RHS 137A. Underside: with prickles.

*Stipules*.—Length: 1.4 cm, serrated. Color: green RHS 137D.

*Auricle*.—Shape: Sword shaped. Length: 3 mm. Width: 1.5 mm at widest point, narrowing to a point. Color: green RHS 137D.

*Vein color*.—Same as leaf color.

*Venation pattern*.—Reticulate.

Wood:

*New wood*.—Color: green RHS 137D. Bark: Smooth.

*Old wood*.—Color: green RHS 137C. Bark: Smooth.

Branching habit:

*Number*.—Few. Main stems cut to allow a flowering stem to shoot — no branching on these. Observation did not ascertain a natural branching habit.

*Lateral branch dimensions*.—N/A.

Stems:

*Mature stem*.—Length: 100 cm. Diameter: 6 mm.

*Internode distance*.—6 cm. The above measurements are all variable, depending on growing conditions in a season.

*Stem pubescence present*.—No.

Prickles:

*Quantity*.—On main canes from base: Ordinary. Number per stem length: 20 per 10 cm. On laterals from main canes: few. Number per stem length: 2 per 10 cm.

*Form*.—Hooked downward.

*Length*.—10 mm.

*Color when young*.—Greyed-red RHS 182C.

*Color when mature*.—Greyed-red RHS 182C.

Small prickles:

*Quantity*.—None.

Disease resistance:

*Mildew*.—Resistant.

*Blackspot*.—Resistant.

*Rust*.—Resistant.

Pest resistance: Not tested.

Winter hardiness: Not tested.

Growing conditions: Normal (green house conditions).

What is claimed is:

1. A new and distinct variety of rose plant of the shrub class suitable for repeat cut-flower production, substantially as herein shown and described.

* * * * *

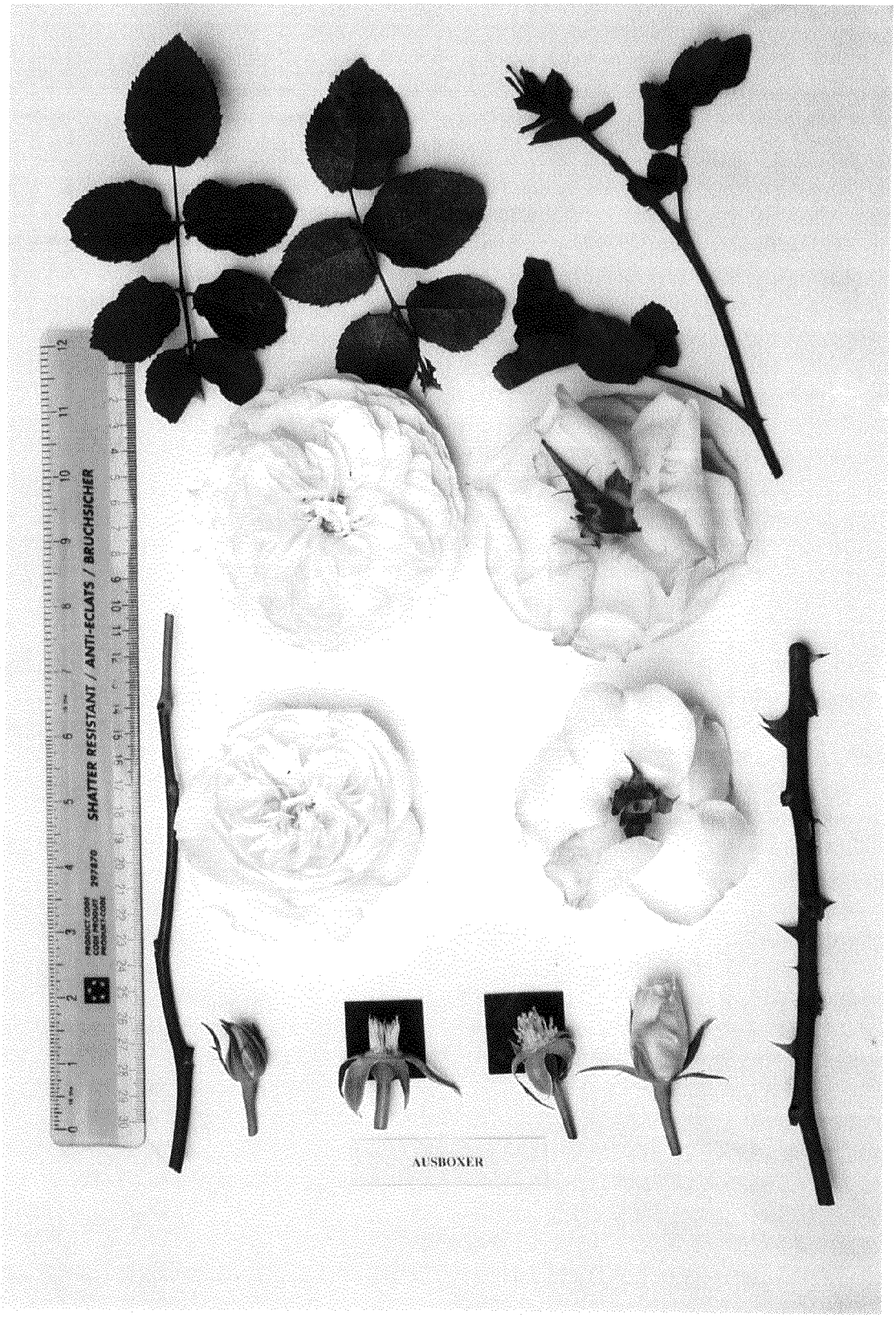
SHATTER RESISTANT / ANTI-ECLATS / BRUCHSICHER
AUSBOXER